United States Patent
De Lamberterie

(10) Patent No.: US 7,795,598 B2
(45) Date of Patent: Sep. 14, 2010

(54) PORTABLE DETECTION DEVICE FOR DETECTING ON THE GROUND ELEMENTS MARKED BY FLUORESCENCE

(75) Inventor: Sébastien De Lamberterie, Paris (FR)

(73) Assignee: Cypher Science, Paris (FR)

( * ) Notice: Subject to any disclaimer, the term of this patent is extended or adjusted under 35 U.S.C. 154(b) by 201 days.

(21) Appl. No.: 11/795,766

(22) PCT Filed: Jan. 12, 2006

(86) PCT No.: PCT/FR2006/000071

§ 371 (c)(1),
(2), (4) Date: Nov. 14, 2007

(87) PCT Pub. No.: WO2006/077304

PCT Pub. Date: Jul. 27, 2006

(65) Prior Publication Data

US 2009/0127475 A1   May 21, 2009

(30) Foreign Application Priority Data

Jan. 21, 2005  (FR) .................................. 05 00648

(51) Int. Cl.
*G01N 21/64* (2006.01)
(52) U.S. Cl. .................................. 250/458.1
(58) Field of Classification Search ............... 250/458.1
See application file for complete search history.

(56) References Cited

U.S. PATENT DOCUMENTS

| | | | |
|---|---|---|---|
| 3,725,694 A * | 4/1973 | D'Amato et al. | 250/485.1 |
| 4,146,792 A * | 3/1979 | Stenzel et al. | 250/365 |
| 6,154,282 A | 11/2000 | Lilge et al. | |
| 6,217,744 B1 * | 4/2001 | Crosby | 205/775 |
| 6,936,827 B1 * | 8/2005 | Mohler | 250/458.1 |
| 2002/0003619 A1 * | 1/2002 | Ahlers et al. | 356/71 |
| 2003/0160182 A1 * | 8/2003 | Petrich et al. | 250/458.1 |

(Continued)

FOREIGN PATENT DOCUMENTS

WO   WO 01/61324 A1   8/2001

(Continued)

OTHER PUBLICATIONS

Silk E, "Led Fluorescence Microscopy in Theory and Practice", Microscope, Carshalton Beeches, US, 2002, pp. 101-118, vol. 50, No. 2-3, XP009034782, ISSN: 0026:282X.

(Continued)

*Primary Examiner*—David P Porta
*Assistant Examiner*—Kiho Kim
(74) *Attorney, Agent, or Firm*—Sughrue Mion, PLLC

(57) ABSTRACT

A portable appliance intended to detect fluorescent particles excited in the visible spectrum for enabling the authentication of products. The appliance comprises: a light source (2) of excitation provided with at least one electroluminescent diode or a laser for producing a focussed light beam: a box (1) for respectively accommodating the light source (2) and means of electrical supply for supplying the light source (2); and compact optical means, whether integrated or not in the box (1), enabling a user to instantaneously visualise the fluorescence of the marked elements excited by means of the light source (2). The appliance is used as a ground detector for authenticating and tracing products comprising a secret marking by fluorescent particles.

23 Claims, 2 Drawing Sheets

U.S. PATENT DOCUMENTS

2005/0083687 A1* 4/2005 Brass et al. .................. 362/231
2006/0152706 A1* 7/2006 Butland ........................ 356/71

FOREIGN PATENT DOCUMENTS

WO    WO 02/10295 A1    2/2002
WO    WO 2004/088387 A1    10/2004

OTHER PUBLICATIONS

Ely Silk, "LED Fluorescence Microscopy in Theory and Practice", *Microscope*, 2002, 101-118, vol. 50: 2/3, Tamarac, FL.

* cited by examiner

PORTABLE DETECTION DEVICE FOR DETECTING ON THE GROUND ELEMENTS MARKED BY FLUORESCENCE

The invention relates to the field of the detection of fluorescent markers by excitation in the visible spectrum and by re-emission in the visible spectrum (0.4-0.7 µm). The invention relates more particularly to a portable device enabling elements marked by fluorescence to be detected on the ground.

Products are increasingly being developed that comprise visibly detectable fluorescent elements, for example bank notes and identity documents. Inks (invisible inks, for example), coatings or other solid or liquid products used in this type of application having a fluorescence that can be detected by UV radiation whose spectrum ranges between approximately 0.01 µm and 0.385 µm, or by IR radiation whose spectrum ranges between 0.76 µm and 1 mm.

Systems for detection by the epifluorescence of an "invisible" ink of the type comprising fluorescent molecules are disclosed in the prior art, particularly in document WO 02/10295 of the same applicant. This detection is generally carried out by means of an epifluorescence microscope comprising a light source emitting in the visible spectrum, combined with a set of filters for causing the excitation of the fluorescent molecules contained in the ink, about a determined wavelength, and for selecting the wavelengths of the emission by fluorescence.

The marking elements enabling each product to be traced secretly may therefore be observed visually by means of an epifluorescence microscope fitted with a dichroic mirror arranged between the eyepiece and the lens. This mirror enables the radiation of a light source to be reflected in the direction of the product forming the support for the marking elements. The marked product is arranged under the lens and may be observed visually through the eyepiece when a suitable set of filters is used that allows the passage of the radiation from the fluorescent molecule used and the light source. The filters are also adapted to the surface of the marked product; in fact it is often necessary to support the contrast between this surface and the fluorescence of the particles to be detected due to the background noise peculiar to the support.

The set of filters makes it possible, in particular, to isolate the photons from the fluorescent emission of the excitation photons emitted by the light source and reflected by the dichroic mirror. A first excitation filter is arranged between the source and the mirror, and a second filter is provided between the mirror and the eyepiece to constitute a stop or emission filter. The excitation filter will encourage the passage of specific wavelengths of the radiation deriving from the selected light source, emitting in the visible spectrum. The stop filter only allows one or more wavelength ranges to pass through within the selected range between 0.4 µm and 0.7 µm. This stop filter is very important because it enables:

the passage of emitted waves to be prevented, i.e. waves not reflected by the dichroic mirror and resulting from the incident light on the marked product and deriving directly from the light source, and the emission waves emitted by the fluorescence to be selected.

Document WO 02/10295 also describes detection systems that enable fluorescence to be observed by epifluorescence without using a microscope. These detection systems incorporate a light source such as a 100 watt mercury vapour lamp housed in a drilled box and equipped with a reflector to reflect the light to the drilled hole. Such a detection system also comprises a set of filters adapted to the characteristics of the fluorescent molecule used and the light source, as well as to the surface of the marked product.

One disadvantage of this type of system is that it still occupies considerable space and uses, in particular, a mercury vapour lamp or other equivalent light generator (halogen/xenon), which prevents its continuous use as a ground detector.

Document WO 2004/088387 discloses a lighting assembly for a laboratory fluorescence microscope. This assembly comprises a box that can be connected to a microscope support structure. This box incorporates a luminous unit consisting of an electroluminescent (light emitting) diode (LED) and an associated optical collimator element in order to route the light produced by the LED, in the form of a (parallel) beam of light rays, to a lateral window of the microscope. The disadvantage of this type of solution is that the space occupied, both laterally and vertically, is still considerable. It is then necessary to provide a structure with a large base for supporting the entire appliance. There is therefore a requirement for more compact tools adapted to routine detections.

A first object of the invention is to propose a detection device of small dimensions (light, portable, preferably capable of being gripped with a single hand) and capable of operating independently (on a battery, for example) for exciting and detecting, exclusively in the visible spectrum, fluorescent particles serving to mark a product.

A second object of the invention is to propose a device that allows rapid, simple detection on the ground, as opposed to the use of laboratory equipment. The invention is therefore designed to facilitate control of the tracing and authentication of secretly marked articles.

For this purpose the invention proposes a portable optical detection appliance for detecting, in a specific marking zone, elements marked by fluorescence, said appliance comprising at least one light source intended for the excitation of particles including a fluorophore function, wherein the light source comprises at least one element for emitting a focussed light beam, consisting of an electroluminescent diode or a laser, each emission element having a similar emission peak around a specific wavelength, characterised in that it comprises:

a box for respectively accommodating the light source, a user interface for controlling the light source and means of electrical supply for supplying the light source, wherein this light source is designed to emit in the visible spectrum and the box comprises a light output orientated towards the marking zone; and optical means, whether or not integrated in the box, comprising a first end that enables the user to detect instantaneously, in the visible spectrum, the fluorescence of marked elements excited in the visible spectrum by means of the light source, a second end opposite to said first end and capable of approaching or lying flush with said marking zone, a filter being provided between these two ends to eliminate at least the radiations with a wavelength shorter than a specific threshold, said ends therefore allowing the passage of the light, for at least one wavelength range in the visible spectrum and being separated by a specific distance that may exceed 2 cm.

Therefore, unlike a cumbersome laboratory assembly, the appliance according to the invention enables all the elements generating the light beam to be grouped in a compact box which incorporates optical means that facilitate visualisation or which is closely associated with these optical means.

According to another embodiment, the light source comprises a plurality of electroluminescent diodes grouped adjacently in an assembly orientated in a direction having a transversal component relative to the axis of alignment of the ends of the optical means.

According to another embodiment, said element for emitting a focussed light beam consists of at least one miniature xenon or halogen bulb associated with a pass band filter to form said light source.

According to another embodiment, the two ends of the optical means are aligned and arranged in the box, which is of a type that can be gripped.

According to another embodiment, box is essentially parallelepipedic, of the pocket-sized type, and comprises on a same side the user interface and said first end of the optical means.

According to another embodiment, the optical means comprise a longitudinal axis corresponding to an axis of visualisation of the elements marked by fluorescence, wherein the distance between the ends of the optical means ranges between 2 and 35 cm.

According to another embodiment, the distance between the ends of the optical means ranges between 2 and 15 cm.

According to another embodiment, the box comprises a housing for receiving batteries enabling the appliance to be used independently, wherein said box comprises a longitudinal axis corresponding to the orientation of the light beam focussed at the level of the light source and has transversally a perimeter of less than 25 cm.

According to another embodiment, at least ten electroluminescent diodes are mounted in a honeycomb arrangement on a support card to form the light source.

According to another embodiment, the electroluminescent diodes are connected to an electronic unit arranged to control the supply to the diodes.

According to another embodiment, the optical means are formed in an essentially cylindrical assembly that can be aligned with an annular device constituting said box, wherein the body of the box forms a crown provided with housings for receiving electroluminescent diodes orientated towards a focal point located on the side opposite the optical means.

According to another embodiment, the box consists of a laser emission device.

According to another embodiment, the laser emission device is of the type having a wavelength of the order of 532 nm to emit a green light beam.

According to another embodiment, the optical means comprise a support means provided with an arm for releasably fixing the laser emission device.

According to another embodiment, the first end of the optical means comprises a perimeter adapted to allow the addition to and/or the integration in the appliance of an optical magnification element enabling the user to visualise better the fluorescence of the marked elements. Fluorescent particles that are not highly visible may therefore be detected, such as fluorescent microspheres with a diameter of less than 5 μm.

According to another embodiment, an excitation filter (of the pass band type) is provided to refine chromatically the emission deriving from the light source.

According to an essential aspect of the invention, the optical means comprise a filter block including an emission filter for preventing at least the passage of the visible waves deriving from the emission element or elements and for allowing the passage of the specific emission wavelengths of the fluorescence of the marked elements.

According to another embodiment, the box comprises a longitudinal axis and at least one alignment of electroluminescent diodes along this longitudinal axis.

Another object of the invention is to propose an application of the portable appliance for rapidly authenticating products having an optically detectable marking zone.

This object is achieved by an application of the appliance according to the invention, characterised in that said portable appliance serves to detect fluorescent particles contained in all or part of a product to be authenticated.

According to another embodiment, said portable appliance serves to detect fluorescent particles contained in a marking zone associated with a product to ensure its marking.

According to another embodiment, the marking zone consists of an adhesion or coating compound comprising a minimum proportion of fluorescent molecules, invisible in daylight but detectable optically by epifluorescence in an excitation wavelength range comprised within the visible spectrum.

According to another embodiment, the fluorescence to be detected derives from at least one thread or fibre 3 to 20 mm in length, called fibrette.

According to another embodiment, the thread or fibrette is associated with a security paper.

According to another embodiment, the fluorescence to be detected derives from bodies of very small size whose volume is less than 0.1 $mm^3$.

According to another embodiment, the fluorescence to be detected derives from microspheres whose diameter ranges between 0.2 and 20 μm.

According to another embodiment, the microspheres are associated with a security paper.

According to another embodiment, the microspheres are dispersed in a lubricating oil or surface treatment of metal parts.

According to another embodiment, the appliance detects luminescent signals of microspheres signalling a DNA hybridisation on DNA bio-chips or chips.

Other embodiments and advantages of this invention will be more clearly evidenced from reading the following description given with reference to the attached drawings, in which.

The invention relates to the detection of any type of product that can be marked by fluorescence. In the following, fluorescent particle must be understood to refer to a particle which absorbs and re-emits respectively in wavelengths in the visible spectrum (0.4-0.7 μm).

The examples of products marked by fluorescence by means of a colourless ink, referred to in document WO 02/10295, may all be the subject of an authentication by means of the ground appliance of this invention. The marked product (6) comprises a specific zone (60) in which elements marked by fluorescence have been inserted. This marking zone (60) may comprise a coating formed by the application of a liquid adhesive or coating product containing fluorescent molecules detectable by epifluorescence. Episcopy is distinguished from diascopy by the fact that in the former the excitation radiation of the object observed does not cross the object, whilst in diascopy the light source lies on the other side of the observed object relative to the observer.

In the following, reference will be made to an example for which the fluorescence of molecules is expressed by an absorption peak at approximately 570 nm. It must be understood that other molecules having a different peak can be used. The fluorescent molecules which the appliance must detect are, for example, invisible to the naked eye on the marked product. The product can no longer be authenticated by classic means using, as in the field of security inks, UV and IR rays. The fluorescent molecules are generally present in low concentration and can only be detected by epifluorescence if on the one hand they are excited by a specific wavelength range of the emission spectrum of a light source, and on the other hand the fluorescence emission is filtered. In other cases the particles are concentrated, but very localised, and can only be detected by epifluorescence when excited by a specific wavelength range of the emission spectrum of a light source on the one hand, and when observed after magnification and filtering of the fluorescence emission on the other.

Figure 1:
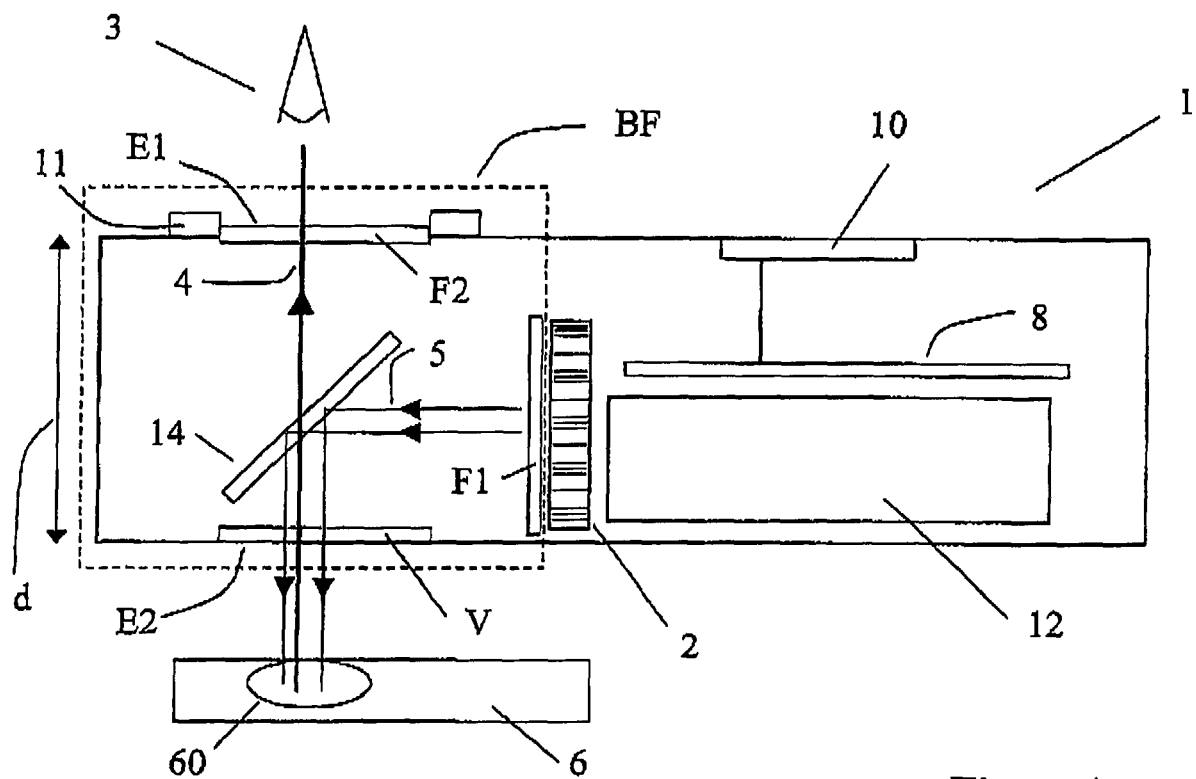
FIG. 1 represents diagrammatically an appliance according to the invention enabling a product marked by means of fluorescent particles to be observed by epifluorescence.

With reference to FIG. 1, the appliance according to the invention comprises a light source (2) that is incorporated in a box (1) of the pocket-sized type and that can easily be gripped. The appliance is therefore easily transportable, unlike equipment of the epifluorescence microscope type. Unlike light sources of the mercury vapour lamp type generally associated with an epifluorescence microscope, the light source (2) considered in the invention is more compact and lighter to allow the use of the appliance on the ground. The portable optical detection appliance is considerably simplified compared to most fluorescence detection appliances and enables elements marked by fluorescence to be reliably authenticated in a specific marking zone (60).

The light source (2) is designed to emit in the visible spectrum. According to the invention, the light source (2) comprises at least one element (organ) for emitting a focussed light beam consisting of an electroluminescent diode (LED) or a laser for exciting the particles having the fluorophore function. For this purpose each emission element has a similar emission peak around a specific wavelength which corresponds essentially to the excitation wavelength of the fluorophores. In one embodiment said element for emitting a focussed light beam (emission element) may consist of at least one miniature xenon or halogen bulb associated with a pass band filter for forming said light source (2).

The excitation of the fluorescent molecules is produced approximately between 0.385 and 0.7 μm, which enables a fluorescent emission to be obtained within a wavelength range belonging to the range of radiations visible with the human eye. This emission is only effected for a light intensity of specific excitation. In the embodiment shown in FIG. 1, the light source (2) comprises a plurality of electroluminescent diodes grouped adjacent to each other. The diode assembly enables a sufficient light intensity to be obtained to excite the fluorophores. At least ten electroluminescent diodes can be mounted in a honeycomb arrangement on a support card to form the light source (2). Consideration may also be given using a single diode of the LED type, which must have the intensity and opening angle characteristics required to generate a luminosity of at least 0.1 lumen.

The appliance is also provided with optical means, whether integrated or not in the box (1). These optical means may comprise magnification means of the microscope type or magnification elements of the type used in a microscope. In one embodiment of the invention the optical means perform a magnification function sufficient to allow the detection of particles of small dimension, 5 μm for example. If the fluorescence is sufficiently intense and the light used is selective, the authentication may be carried out without such magnification means. The latter may therefore be omitted and a magnification accessory may nevertheless be associated with the optical means if appropriate. As illustrated in FIG. 1, the optical means comprise, for example, a first end (E1) enabling the user to visualise instantaneously the fluorescence of the marked elements, and a second opposite end (E2) capable of approaching or lying flush with the marking zone (60). The ends (E1, E2) are, for example, aligned and allow the passage of the light, for at least one wavelength range in the visible spectrum. The marking is detected by direct observation of the surface of the product through optical means without destruction or deterioration of the surface of the product concerned. The first end (E1) of the optical means may comprise a perimeter (11) adapted to allow the addition to and/or integration with the appliance of an optical magnification element which may be considered necessary to enable the user to visualise the fluorescence of the marked elements. In particular, it is permissible with such an optical magnification element to detect (or better distinguish) small fluorescent particles.

The diode assembly illustrated in FIG. 1 is orientated in a direction having a transversal component relative to the axis of alignment of the ends (E1, E2) of the optical means. The trajectory of the excitation radiation (5) derived from the light source (2) passes through an excitation filter (F1), for example, provided to refine the emission chromatically, and is then reflected by a mirror (14) of the dichroic type. The mirror (14) reflects this radiation in the direction of the marking zone (60) formed on the support in order to illuminate above this zone (60). The marked product is arranged under the second end and may be observed visually, as shown by the reference (3). The excitation filter (F1) encourages the passage of the specific wavelengths of the radiation deriving from the selected light source emitting in the visible spectrum. These wavelengths will be determined as a function of the fluorochrome, i.e. as a function of the fluorescent material selected to produce, under a given excitation wavelength of the visible spectrum, a fluorescent emission wavelength in the spectrum of the visible light rays. The dichroic mirror (14) is adapted to the two excitation and emission wavelength spectra.

In the embodiment shown in FIG. 1, the box (1) of the portable detection appliance may be advantageously gripped and enables not only the light source (2) but also the optical means to be housed with a suitable filter block (BF). A user interface (10) for controlling, in particular, the light source (2) and the electrical supply means for supplying the light source (2), are also arranged in the box (1). The housing (12) enables batteries (9V PP3 or similar) to be received for independent use of the appliance (which is thus autonomous). This compact box (1) may therefore delimit the entire appliance, which makes it easy to handle. In one embodiment of the invention, the box (1) comprises a longitudinal axis corresponding to the orientation of the focussed light beam at the level of the light source (2), and has, transversally, a perimeter of less than 25 cm. The ends (E1, E2) of the optical means are, for example, separated by a specific distance (d, d') of the order of a few centimeters, which may exceed 2 cm (a distance of approximately 4 cm being sufficient). The distance (d) may of course be shorter for embodiments in which said optical means are external to the box including the light source (2). According to certain embodiments of the invention, the optical means comprise a longitudinal axis corresponding to a visualisation axis of the elements marked by fluorescence, and the distance (d') between the ends of the optical means ranges between 2 and 35 cm. This distance (d, d') ranges between 2 and 15 cm, for example. The first end (E1) may comprise a filter (F2), a red filter, for example, when the excitation extends beyond 600 nm, the excitation filter (F1) being a green filter, for example, the red filter thus constituting a emission filter. In particular, this filter (F2) enables the photons of the fluorescent emission (4) of the excitation photons (5) emitted by the light source (2) and reflected by the mirror (14) to be isolated. It is then easy to visualise the fluorescence of molecules having an emission peak at 605 nm, for example.

It will be understood that the optical means may comprise a filter block (BF) that includes such an emission filter (F2) for filtering the specific emission wavelengths of the fluorescence of the marked elements. This allows the visualisation of the fluorescent particles in the marking zone (60). The emission filter (F2) arranged between the two ends (E1, E2) enables at least the radiations with a wavelength lower than a particular threshold. In practice this filter (F2) therefore enables the excitation radiations to be filtered so that only the emission radiations in the visible spectrum of the marked elements are able to pass through. In embodiments in which the excitation radiation is rendered monochromatic, thanks to the first excitation filter (F1), for example, this second filter (F2) may be omitted. If fluorescences emitting in the UV spectrum are observed by epifluorescence (unlike in this invention), the emission filter (F2) is not required. In fact, since the excitation waves are hardly visible, the reflection of the excitation waves does not impair the observation of the emitted waves deriving from the fluorescence.

The user interface (10) may comprise at least two buttons that both enable diodes of the LED type to be switched on for simple illumination to facilitate positioning in the marking zone (60), and also enable the diode assembly to be switched on to allow the fluorophores in the marking zone (60) to be excited. To allow these different types of illumination, the electroluminescent diodes are connected to an electronic processing unit (8) provided to control the electrical supply to the diodes. In the example of particles having an excitation peak at 570 nm, a red light derived from one or more delocalised sources therefore allows positioning in the zone (60), and a green light enables the fluorophores to be excited. The delocalised sources are arranged outside the optics but in the box (1), for example in a position adjacent to the glass forming the second end (E2). This glass (or similar transparent element) may be anti-reflective to improve visualisation by limiting the losses due to the reflection of the excitation and emission rays.

As shown in FIG. 1, the box (1) is essentially parallelepipedic, of the pocket-sized type, and comprises on the same side the user interface (10) and said first end (E1) of the optical means.

The optical means allow a specific magnification, which may be a function of the size of the particles to be observed. These particles consist, for example, of microspheres (having a diameter that may range between 0.2 and 20 µm), for example of the type described in patent WO 01/30936 of the same applicant. The number of LED diodes as well as the magnification of the optics depend on the size of the microspheres to be observed; a lens with an ×10 magnification may be provided, for example, to detect microspheres of the order of 10 µm. In the embodiment in the figure, the lens (not shown) may be an element distinct from the box (1), so that the box (1) is suitable for any type of fluorescent molecules when the suitable lens is used additionally. The lens may be arranged against the second end (E2) of the optical means.

Figure 2:
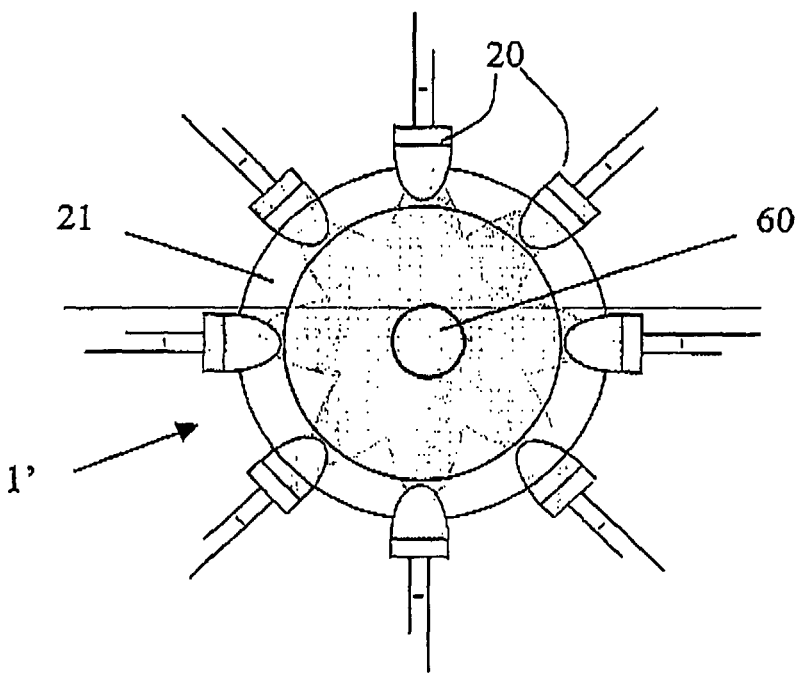
FIG. 2 represents an arrangement of diodes of the LED type (Light-Emitting Diode) in a crown.

With reference to FIG. 2, the optical means are formed in an essentially cylindrical assembly that can be aligned with an annular device constituting said box (1'). In this embodiment, the body (21) of the box (1') forms a crown (21) provided with housings for receiving electroluminescent diodes (20) orientated towards the centre of the crown. The housings of the body (1') may be inclined in the direction of a lower side of the crown, whilst the optical means are arranged on the upper side of the crown (21).

With the arrangement of diodes in a crown, the diodes (LEDs) are focussed on the same point in order to increase the quantity of light in the marking zone (60) to be observed. This arrangement enables the fluorophores in the marking zone, or body to be observed, to be excited. For microspheres from 8 to 10 µm, an ×10 magnification lens may be used and the crown (21) will comprise 4 focussed LEDs. To visualise smaller microspheres, 5 µm for example, it is preferable to use a system comprising 8 focussed LEDs with a higher magnification lens, ×45 for example. However, the number of diodes may vary as a function of the intrinsic characteristics of each diode (luminosity, opening angle, level of supply). Blue LEDs with peak emission around 470 nm may be suitable for detecting fluorescent molecules having their absorption peak at 570 nm, even if the excitation is then 30% of its maximum. Since the emission spectrum of the blue LEDs does not exceed 600 nm, it is possible to dispense with an excitation filter (F1) by using an emission filter of the high pass band type at 610 nm. In embodiments with a crown (21), an excitation filter may also be considered, the filter (F1) then being annular (not shown) or comprising a plurality of filters each associated with one or more diodes (20). The arrangement with a crown or similar shape (truncated cone, pyramid, etc.) allows considerable flexibility for associating with optical means provided with varying magnification.

One embodiment of the invention will now be described in considerable detail with reference to FIG. 3.

Figure 3:
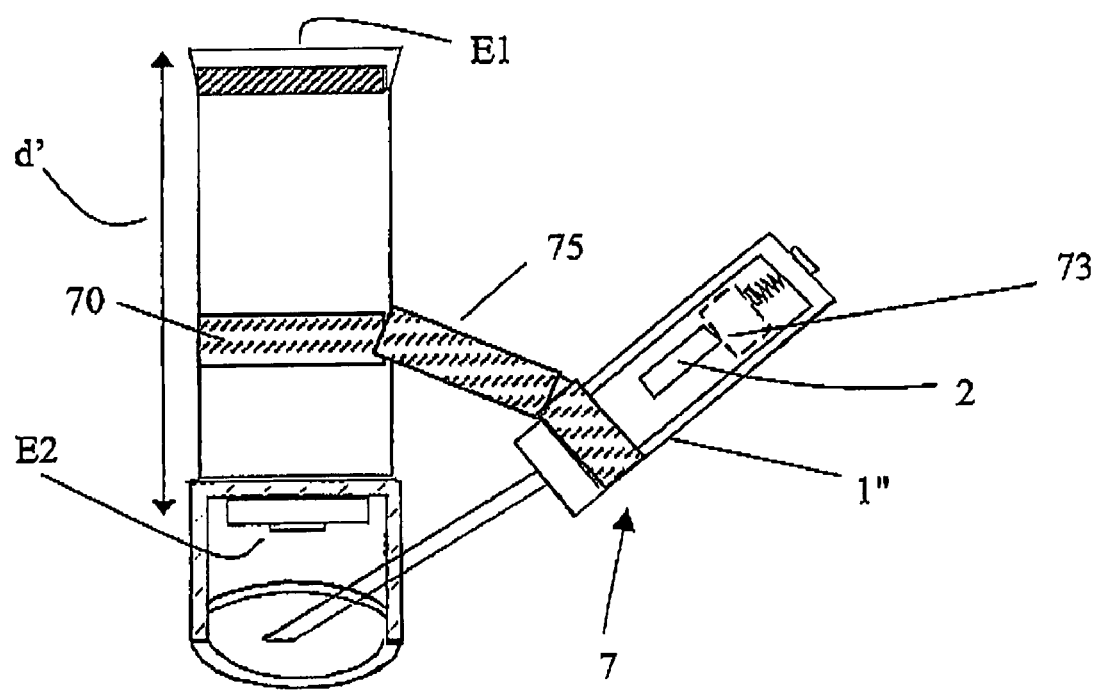
FIG. 3 represents diagrammatically an appliance according to the invention provided with a light source of the laser type.

The box (1") consists of a laser emission device (17) in the example shown in FIG. 3. The pump circuit (73) of the laser emission device is adjusted to a wavelength with a peak at around 532 nm to generate a green light. A laser emission device of the type having a wavelength of the order of 532 nm may be suitable for effectively exciting molecules having an absorption peak at approximately 570 nm.

The optical means used with the laser emission device (7) may comprise a support means (70) provided with an arm (75) for releasably fixing the box (1") incorporating the laser light source (2). The use of a source of the laser type provides an illumination that can be focussed on a small surface area (with a diameter of less than 5 mm), and the box (1") of the cylindrical type, containing the laser source, occupies very little space. The box (1") then has a size comparable to a pen. Such an application is advantageous for observing bodies of very small size, for example microspheres having a diameter of between 0.2 and 5 µm.

The wavelength of the green lasers of the type emitting at 532 nm enables a family of fluorescent molecules to be excited, these molecules being excited around 570 nm and emit beyond 610 nm (red wavelength). The excitation at 532 nm is certainly not the optimum because the absorption peak is at 570 nm. Nevertheless the luminous power of the lasers may compensate for the difference between the emission peak of the source and the absorption peak (to the extent that there is an overlap). Moreover, the chromatic precision of a laser emission device (7) obviates the need to use excitation filters (F1), which are required when using green or white LEDs, for example, as light sources.

In this embodiment the optical means may consist of a conventional lens, with or without eyepiece, and without emission filter. The lens may be similar to those used as a magnification element of a microscope.

The laser emission device (7) may be of the current type having a power of less than 5 mW in order to conform to the security standards. By way of non-exhaustive example, the laser emission device (7) comprises a laser diode from Sony, generating a constant wave whose wavelength is 532 nm. It has an output power of 4.99 mW and a service life of the order of 2000 to 3000 hours. The box (1") also comprises a housing for at least one battery and 2 AAA type batteries, for example.

Figure 4:
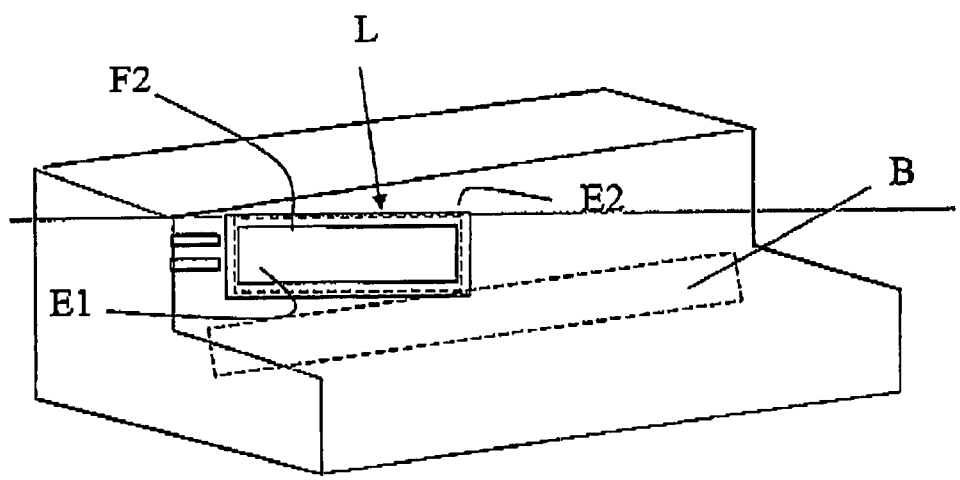
FIG. 4 shows an example of an appliance with electroluminescent diodes in an embodiment of the invention.

FIG. 4 illustrates an embodiment in which the box comprises a longitudinal axis and at least one alignment of electroluminescent diodes along this longitudinal axis. A bar (B) of LEDs may be incorporated in the box and supplied by batteries or by a main supply, a user interface enabling the illumination/extinction of the light source thus constituted to be controlled. The optical means may consist of a device of the microscope type (L), to which is associated an emission filter (F2). The device of the microscope type or a similar magnification means may be rendered integral with and articulated to a box. An excitation filter (not shown) may possibly be provided, for example in a position adjacent to the bar (B) of electroluminescent diodes. The box may comprise an L-profile with a support section for placing the product to be authenticated and a lateral section in which the light source is arranged.

With the portable detection appliance it is possible to detect a security marking by exciting the fluorescent molecules directly on a textile manufactured from oiled threads. The fluorophore is previously inserted in the oil covering the thread.

It must be understood that the invention proposes an appliance that enables markings to be detected in various fields, for example for works of art, textiles, hollow or flat glass (by surface treatment, screen printing, or by ink jet), characters and drawings printed by heat transfer, offset or heliogravure, spare metal parts (by surface treatment or by the use of a lubricating oil), aluminium blisters and holograms (by heliogravure or flexography), security papers, bank notes and scaling papers of the fiscal wrapping type. Security paper is understood to refer, for example, to art papers such as cheques, bonds, identity documents, labels, fiscal wrappings or any other paper that is intended to be unfalsifiable. An application of the appliance may be considered in the field of molecular biology, in particular for the detection of fluorescent microspheres signalling DNA hybridisation on DNA bio-chips or chips. These fluorescent microspheres then serve as a marker for fixing on at least one hybridised DNA strand. For this type of application only the hybridised DNA strands may be fixed on the fluorescent microspheres, by a biotin-streptavidin link, for example.

The portable optical detection appliance allows simple visualisation of the fluorescent particles contained in all or part of a product to be authenticated, for example in a marking zone (60) associated with a product. The user simply needs to press a button of the interface (10) to excite the fluorescent particles. The marking zone (60) formed on the support to be observed with the appliance consists, for example, of an adhesion or coating compound, for example invisible inks, comprising a minimum proportion of fluorescent molecules.

These molecules, for example molecules incorporated in bodies of very small size having a volume of less than 0.1 mm$^3$, in microspheres of a few microns in diameter, are invisible in daylight but are detectable optically by epifluorescence within an excitation wavelength range comprised within the visible spectrum. The appliance according to the invention therefore advantageously constitutes a ground detector for authenticating products containing a secret marking by fluorescent particles. This detection may be carried out quickly in situ without having to send the product to a laboratory equipped with heavy equipment of the epifluorescence microscope type.

The fluorescence to be detected may also be incorporated in at least one thread or small fibre called fibrette. The detection may therefore be made for fluorescent particles impregnating or overlapping at least one thread or fibrette associated with a product to ensure that it is marked. Such a thread or fibrette is associated, for example, with a security paper. As a variant the fluorescence to be detected may derive from microspheres. Patent application WO 01/30936 of the same applicant describes a specific example of microspheres having connections to fluorescent molecules. Such fluorescent microspheres may also be associated with a security paper, bank notes, sealing papers, polymer-based materials or other types of support or medium such as leather, textile, etc. Such fluorescent microspheres may also be dispersed in a lubricating oil or surface treatment of metal parts.

It will be understood that the visualisation may also be satisfactorily achieved by means of optical means of the appliance according to the invention, directly by the human eye (3) or by means of a device of the digital camera type, for example a CCD camera (Charge Coupled Device), which may possibly be fixed on the side of the first end (E1) of the optical means to allow visualisation of the zone (60) to be observed on a screen. A photosensitive cell also enables the detection to be carried out due to its sensitivity to photons. Detection without visualisation may also be considered, a detection signal being expressed acoustically (connection to an alarm) or by a luminosity measurement.

It must be evident to persons skilled in the art that this invention allows embodiments in numerous other specific forms without detracting from the scope of the invention as claimed.

The invention claimed is:

1. A portable optical detection appliance for detecting, in a specific marking zone (60), elements marked by fluorescence, said appliance comprising at least one light source (2) intended for the excitation of particles including a fluorophore function, wherein the light source (2) comprises at least one element for emitting a focussed light beam, consisting of an electroluminescent diode or a laser, each emission element having a similar emission peak around a specific wavelength, characterised in that it comprises:
   a box (1, 1', 1") for respectively accommodating the light source (2),
   a user interface (10) for controlling the light source and means of electrical supply for supplying the light source (2), wherein the light source is designed to emit in the visible spectrum and to illuminate the marking zone (60) directly and the box (1, 1', 1") comprises a light output orientated towards the marking zone (60); and
   optical means, whether or not integrated in the box (1, 1', 1"), comprising a first end (E1) that enables the user to detect instantaneously, in the visible spectrum, the fluorescence of marked elements excited in the visible spectrum by means of the light source (2), a second end (E2) opposite to said first end and capable of approaching or lying flush with said marking zone (60), a filter (F1) being provided between these two ends (E1, E2) to eliminate at least the radiations with a wavelength shorter than a specific threshold, said ends (E1, E2) therefore allowing the passage of the light, for at least one wavelength range in the visible spectrum and being separated by a specific distance (d) that may exceed 2 cm.

2. The appliance according to claim 1, in which the two ends (E1, E2) of the optical means are aligned and arranged in the box (1, 1', 1"), which is of a type that can be gripped.

3. The appliance according to claim 1 or 2, in which the box (1) is essentially parallelepipedic, of the pocket-sized type, and comprises on a same side the user interface (10) and said first end (E1) of the optical means.

4. The appliance according to claim 1 or 2, in which the optical means comprise a longitudinal axis corresponding to an axis of visualisation of the elements marked by fluorescence, wherein the distance (d') between the ends of the optical means ranges between 2 and 35 cm.

5. The appliance according to claim 1 or 2, in which the distance (d) between the ends (E1, E2) of the optical means ranges between 2 and 15 cm.

6. The appliance according to claim 1, characterised in that the optical means are formed in an essentially cylindrical assembly that can be aligned with an annular device constituting said box (1'), wherein the body (21) of the box (1') forms a crown provided with housings for receiving electroluminescent diodes orientated towards a focal point located on the side opposite the optical means.

7. The appliance according to claim 1, characterised in that said element for emitting a focussed light beam consists of at least one miniature xenon or halogen bulb associated with a pass band filter to form said light source (2).

8. The appliance according to claim 1, characterised in that the box (1") consists of a laser emission device (7).

9. The appliance according to claim 8, in which the laser emission device (7) is of the type having a wavelength of the order of 532 nm to emit a green light beam.

10. The appliance according to claim 8, in which the optical means comprise a support means (70) provided with an arm (75) for releasably fixing the laser emission device (7).

11. The appliance according to claim 1, in which the first end (E1) of the optical means comprises a perimeter (11) adapted to allow the addition to and/or the integration in the appliance of an optical magnification element enabling the user to visualise better the fluorescence of the marked elements.

12. The appliance according to claim 1, in which an excitation filter (F1) is provided to refine chromatically the emission deriving from the light source (2).

13. The appliance according to claim 1, characterised in that the box comprises a longitudinal axis and at least one alignment of electroluminescent diodes along this longitudinal axis.

14. An application of the appliance according to claim 1, characterised in that said portable appliance serves to detect fluorescent particles contained in all or part of a product to be authenticated.

15. The application of the appliance according to claim 14, in which said portable appliance serves to detect fluorescent particles contained in a marking zone (60) associated with a product to ensure its marking.

16. The application of the appliance according to claim 14, in which the marking zone consists of an adhesion or coating compound comprising a minimum proportion of fluorescent molecules, invisible in daylight but detectable optically by epifluorescence in an excitation wavelength range comprised within the visible spectrum.

17. The application of the appliance according to claim 14, in which the fluorescence to be detected derives from at least one thread or fibre 3 to 20 mm in length, called fibrette.

18. The application of the appliance according to claim 17, in which the thread or fibrette is associated with a security paper.

19. The application of the appliance according to claim 14, in which the fluorescence to be detected derives from bodies of very small size whose volume is less than 0.1 $mm^3$.

20. The application of the appliance according to claim 14, in which the fluorescence to be detected derives from microspheres whose diameter ranges between 0.2 and 20 µm.

21. The application of the appliance according to claim 20, in which the microspheres are associated with a security paper.

22. The application of the appliance according to claim 20, in which the microspheres are dispersed in a lubricating oil or surface treatment of metal parts.

23. The application of the appliance according to claim 14, in which the appliance detects luminescent signals of microspheres signalling a DNA hybridisation on DNA bio-chips or chips.

* * * * *